United States Patent
Koros et al.

(10) Patent No.: US 9,335,782 B2
(45) Date of Patent: May 10, 2016

(54) RATCHET MECHANISM INCLUDING LOCKABLE PINION ASSEMBLY

(76) Inventors: Tibor B. Koros, Moorpark, CA (US); Gabriel J. Koros, Moorpark, CA (US)

( * ) Notice: Subject to any disclaimer, the term of this patent is extended or adjusted under 35 U.S.C. 154(b) by 2247 days.

(21) Appl. No.: 12/284,464

(22) Filed: Sep. 22, 2008

(65) Prior Publication Data

US 2009/0100960 A1   Apr. 23, 2009

Related U.S. Application Data

(63) Continuation-in-part of application No. 29/292,659, filed on Oct. 22, 2007, now Pat. No. Des. 565,932.

(51) Int. Cl.
| | |
|---|---|
| G05G 1/08 | (2006.01) |
| G05G 5/02 | (2006.01) |
| G05G 5/18 | (2006.01) |
| A61B 17/02 | (2006.01) |
| A61B 17/00 | (2006.01) |

(52) U.S. Cl.
CPC ............. *G05G 1/082* (2013.01); *A61B 17/02* (2013.01); *G05G 5/02* (2013.01); *G05G 5/18* (2013.01); *A61B 2017/00407* (2013.01); *Y10T 74/2069* (2015.01); *Y10T 74/2133* (2015.01)

(58) Field of Classification Search
USPC .......... 74/422, 89.11, 842, 30, 530, 531, 532, 74/533, 536; 600/201, 213, 215, 222, 226, 600/230, 234; 254/95, 96, 97, 103, 112; 292/160, 172, 142; 606/218, 205, 142, 606/175.1
See application file for complete search history.

(56) References Cited

U.S. PATENT DOCUMENTS

| | | | | |
|---|---|---|---|---|
| 1,607,667 | A | * | 11/1926 | Essen ................................ 74/422 |
| 4,718,151 | A | * | 1/1988 | LeVahn et al. ................ 600/228 |
| 4,724,692 | A | * | 2/1988 | Turin et al. ...................... 70/225 |
| 5,067,477 | A | * | 11/1991 | Santangelo ..................... 74/422 |
| 5,167,223 | A | * | 12/1992 | Koros et al. ..................... 74/422 |
| 5,795,291 | A | * | 8/1998 | Koros et al. ................... 600/213 |
| 5,846,193 | A | * | 12/1998 | Wright ........................... 600/215 |
| 5,944,658 | A | * | 8/1999 | Koros et al. ................... 600/232 |
| 5,961,186 | A | * | 10/1999 | Phillips ....................... 301/124.2 |
| 6,896,654 | B2 | * | 5/2005 | Paolitto et al. ................ 600/232 |
| 2004/0199055 | A1 | * | 10/2004 | Mulac et al. .................. 600/226 |
| 2006/0247649 | A1 | * | 11/2006 | Rezach et al. .................. 606/90 |
| 2008/0312509 | A1 | * | 12/2008 | Jacobson et al. ............. 600/230 |

* cited by examiner

*Primary Examiner* — Daniel Yabut
(74) *Attorney, Agent, or Firm* — Fulwider Patton LLP

(57) ABSTRACT

A manually operable ratchet mechanism includes a pinion assembly comprised of a handle connected to a shaft. The handle and shaft are mounted on a housing to allow the shaft to be rotated as a consequence of a user manually rotating the handle. The shaft carries a pinion configured to engage a toothed rack to incrementally move the rack in discrete steps relative to the housing. Additionally, a rotatable detent member is provided which rotates with the shaft as the handle is rotated. The rotatable detent member cooperates with a fixed detent member on the housing to define discrete detent positions which provide discrete step tactile feedback to the user. The handle is mounted for (1) axial rotation with respect to the shaft axis and additionally for (2) pivotal movement between locked and unlocked positions around a pivot axis oriented substantially perpendicular to the shaft axis. In the unlocked position, the shaft and rotatable detent member can rotate relative to the housing as the handle is turned. In the locked position, the rotatable detent member is forced into firm engagement with the fixed detent member to prevent axial rotation of the shaft.

20 Claims, 2 Drawing Sheets

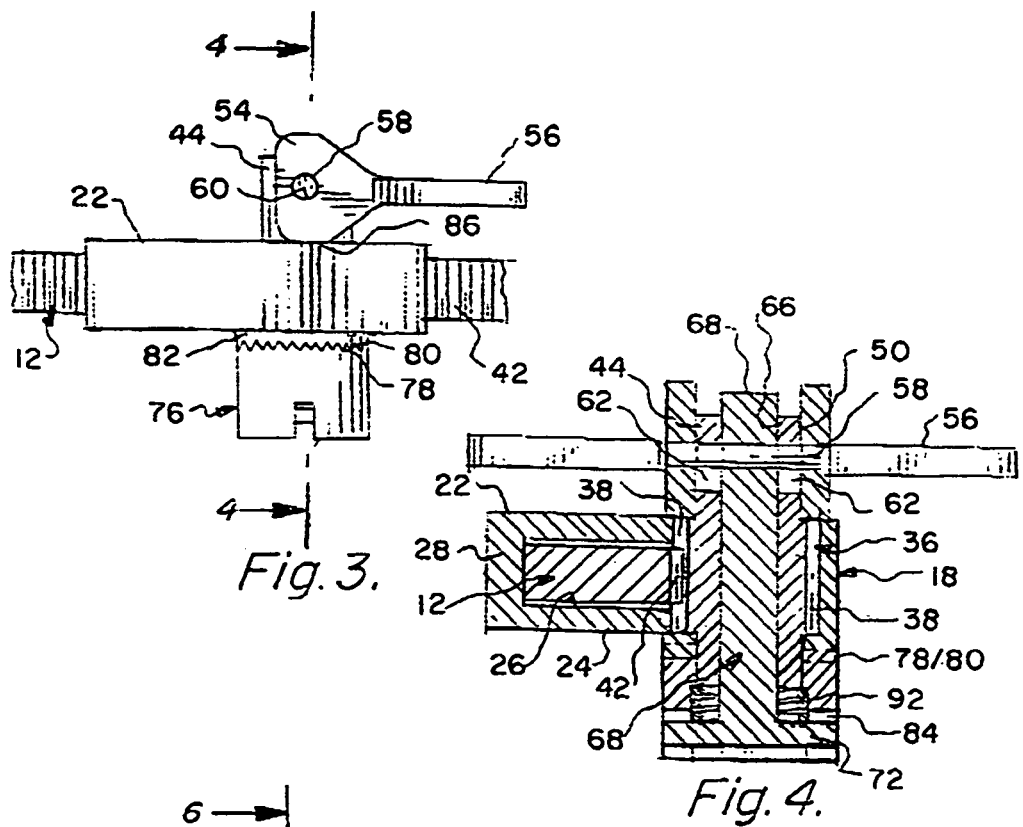
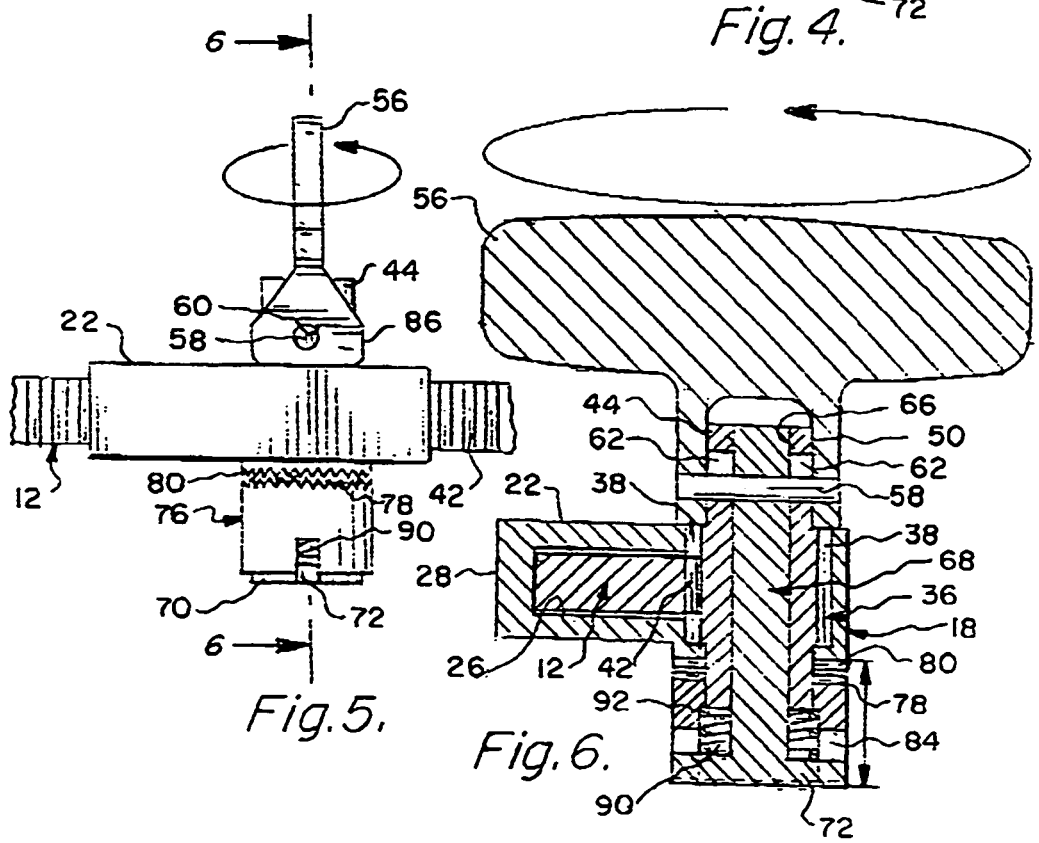

RATCHET MECHANISM INCLUDING LOCKABLE PINION ASSEMBLY

RELATED APPLICATIONS

This application is a C.I.P. of U.S. Design application 29/292,659 filed Oct. 22, 2007.

FIELD OF INVENTION

This invention relates generally to manually operable ratchet mechanisms.

BACKGROUND OF THE INVENTION

Manually operable ratchet mechanisms are used in a wide variety of devices for various applications for incrementally moving a mechanical member. For example only, such mechanisms are often employed in retractor instruments useful in surgical procedures for moving neighboring bone segments; e.g., see U.S. Pat. No. 6,431,025 issued Aug. 13, 2002.

SUMMARY OF THE INVENTION

A manually operable ratchet mechanism in accordance with the invention includes a pinion assembly comprised of a handle connected to a shaft. The handle and shaft are mounted on a housing to allow the shaft to be rotated axially as a consequence of a user manually rotating the handle. The shaft carries a pinion configured to engage a toothed rack to incrementally move the rack in discrete steps relative to the housing. Additionally, a rotatable detent member is provided which rotates with the shaft as the handle is rotated. The rotatable detent member cooperates with a fixed detent member on the housing to define discrete detent positions which provide discrete step tactile feedback to the user as the handle is rotated.

In a preferred embodiment of the invention, the handle is mounted for (1) axial rotation with respect to the shaft axis and additionally for (2) pivotal movement between locked and unlocked positions around a pivot axis oriented substantially perpendicular to the shaft axis. In the unlocked position, the shaft and rotatable detent member can axially rotate relative to the housing as the handle is turned. In the locked position, the rotatable detent member is forced into firm engagement with the fixed detent member to prevent axial rotation of the shaft.

In accordance with one aspect of the preferred embodiment, the shaft is tubular and defines an axial passageway for accommodating an axially movable locking member, e.g., rod. A first end of the rod is connected to the handle and a second rod end carries a radial finger for engaging the rotatable detent member. When the handle is in the unlocked position, a spring acts to loosely engage the rotatable detent member against the fixed detent member with an axial force sufficiently light to permit the detent members to rotate relative to one another. In contrast, when the handle is in the locked position, the rod is lifted to cause the radial finger to exert a firm axial force against the rotatable detent member to lock it against the fixed detent member and thus inhibit rotation of the rotatable detent member and shaft.

In accordance with a further aspect of the preferred embodiment, the rotatable detent member is cylindrical and has an end surface carrying multiple detents, e.g., a series of V-shaped teeth. The rotatable detent member teeth are located to mate with one or more detents, e.g., a corresponding series of V-shaped teeth, on the fixed detent member. The respective detents on the rotatable detent member and the fixed detent member mutually engage to permit discrete stepped rotation of the rotatable detent member and shaft when the handle is in the unlocked position and to prevent such rotation movement when the handle is in the locked position.

In accordance with a still further aspect of the preferred embodiment, the handle includes a cam surface configured to move the rod axially as the handle is moved from said unlocked position to said locked position to cause the radial finger to axially press against the rotatable detent member.

BRIEF DESCRIPTION OF THE DRAWINGS

FIG. 3 is a side view of the ratchet mechanism of FIG. 1 shown in its locked position;

FIG. 4 is an enlarged sectional view taken substantially along the plane 4-4 of FIG. 3;

FIG. 5 is a side view of the ratchet mechanism of FIG. 1 shown in its unlocked position; and FIG. 6 is an enlarged sectional view taken substantially along the plane 6-6 of FIG. 5.

DETAILED DESCRIPTION OF THE DRAWINGS

Figure 1:
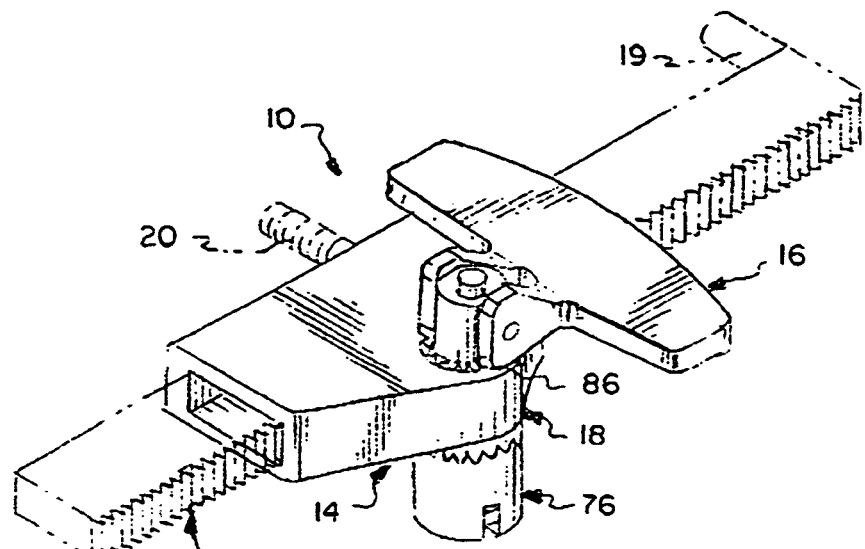
FIG. 1 is an isometric view of a ratchet mechanism in accordance with the invention incorporating a preferred lockable pinion assembly.

Attention is initially directed to FIG. 1 which depicts a preferred ratchet mechanism 10 in accordance with the present invention. The mechanism 10 is comprised of a toothed rack 12 and a pinion assembly 14. The pinion assembly 14 includes a handle 16 mounted on a housing 18. As will be discussed in detail hereinafter, the handle 16 is mounted for selective placement in a locked position (as depicted in FIG. 1) or an unlocked position. When in the unlocked position, the handle 16 can be manually rotated, e.g. clockwise, to move the rack 12 linearly in a first direction relative to the housing 18, or rotated oppositely, e.g., counter clockwise, to move the rack 12 linearly in an opposite direction. To facilitate a user's ability to precisely incrementally move the rack 12 relative to the housing 18, the pinion assembly 14 preferably defines discrete detent positions which provide discrete step tactile feedback to the user as the handle 16 is rotated. FIG. 1 also shows in phantom optional posts 19, 20 which can be respectively coupled to the rack 12 and housing 18. The posts 19, 20 can be used in a variety of applications to move external members, e.g., bone segments, relative to one another.

Figure 2:
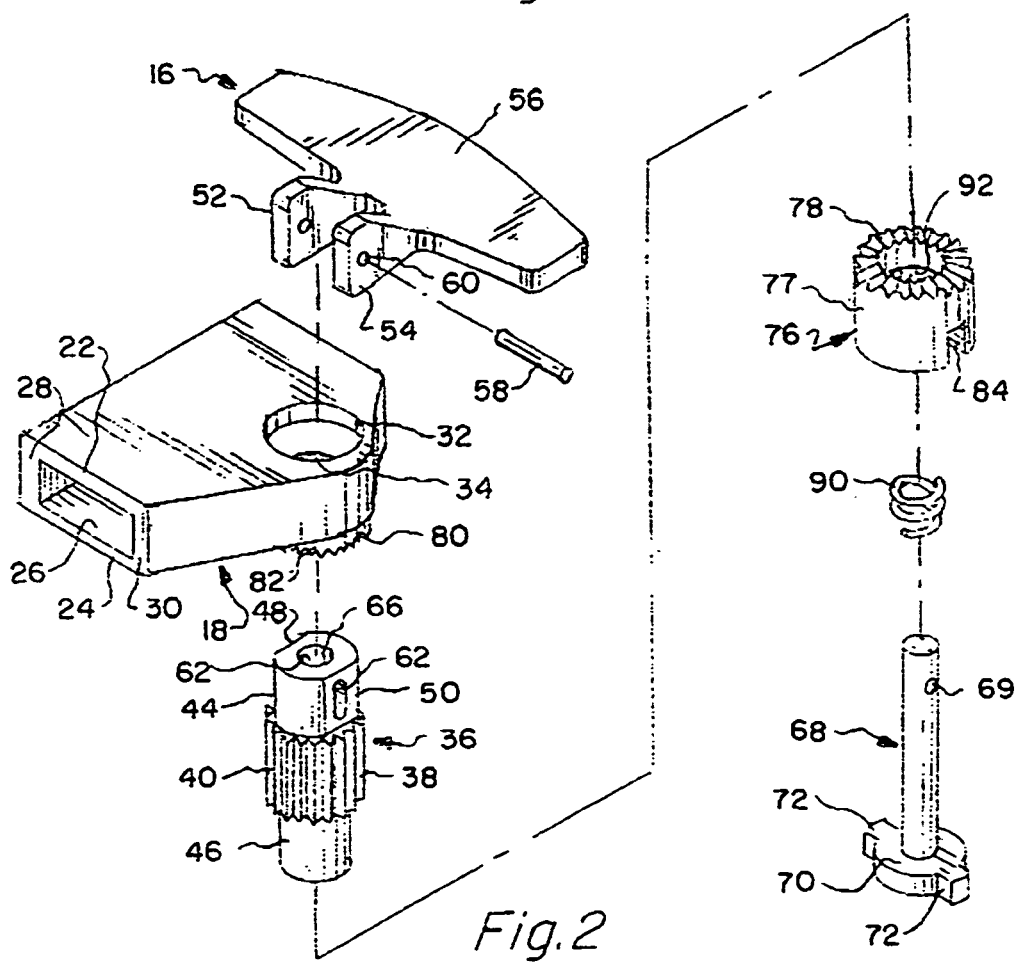
FIG. 2 is an exploded isometric view of the pinion assembly of FIG. 1.

Attention is now directed to FIG. 2 which shows an exploded view of a preferred embodiment of the pinion assembly 14. The pinion assembly 14 includes a housing 18 comprised of an upper wall 22 and a lower wall 24 spaced from one another to define a channel 26 therebetween. First and second side walls 28 and 30 bound the channel 26 which is dimensioned to closely accommodate the rack 12 for linear movement therethrough.

Aligned openings 32 and 34 are formed in the upper and lower walls 22 and 24 for receiving a shaft 36. The shaft 36 carries a pinion 38 having teeth 40 dimensioned and located to engage the teeth 42 on rack 12. The shaft 36 includes an upper portion 44 projecting axially above the pinion 38 and a lower portion 46 projecting axially below the pinion 38. More particularly, the shaft is configured for mounting in housing 18 so as to locate a portion of pinion 38 between the upper and lower walls 22 and 24 (FIGS. 4, 6) with the shaft portion 44 extending upwardly through upper wall opening 32 and the shaft portion 46 extending downwardly through lower wall opening 34.

The shaft 36 essentially comprises a circular cylinder cut to define the pinion 38 and upper and lower shaft portions 44 and 46. The upper portion 44 is preferably cut to define flat surfaces 48 and 50 for fitting between ears 52 and 54 projecting from a flat key portion 56 of handle 16. A pin 58 extends through holes 60 in the ears 52 and 54 and through axially elongated holes 62 in the flat surfaces 48 and 50 to allow the handle 16 to pivot around pin 58.

The shaft 36 is preferably tubular defining a central axial passageway 66 for accommodating a locking member or rod 68. The rod 68 includes a lateral through hole 69 configured for alignment with ear holes 60 and shaft holes 62 for accommodating pin 58. The rod 68 carries a flange 70 at its lower end defining one or more radial fingers 72.

A rotatable detent member 76 comprising a tubular cylinder 77 is mounted on the rod 68 above the flange 70. The upper edge of detent member 76 carries multiple discrete detents, e.g., V-shaped teeth, 78. The teeth 78 are intended to engage detents 80 formed on a fixed detent member 82 located on the outer surface of the lower housing wall 24 around shaft opening 34. As will be discussed hereinafter, the handle 16 is mounted for pivotal movement around the axis defined by pin 58 between a locked position and an unlocked portion. When the handle is in the locked position (i.e., FIG. 3 with key portion 56 oriented horizontally), the teeth 78 of the rotatable detent member 76 are firmly engaged against the detents 80 on the fixed detent member 82 thus inhibiting rotation of the shaft 36, thereby preventing pinion 38 from linearly moving the rack 12. On the other hand, when the handle 16 is in its unlocked position (i.e., FIG. 5 with key portion 56 oriented vertically), the rotatable detent member 76 is allowed to move relative to the fixed detent member 82 thus allowing rotation of the pinion 38 to cause linear movement of the rack 12.

As will become apparent hereinafter, the assembly 14 will be locked when the handle 16 pulls the rod 68 upwardly through the shaft 36 to allow move the radial finger 72 to move axially in keyway 84 to firmly near against the rotatable detent member 76. On the other hand, if the finger 72 is not axially moved sufficiently to firmly bear against the rotatable detent member 76, then the assembly 14 will remain in an unlocked state allowing rotation of the shaft 36 and pinion 38.

More particularly, note in FIGS. 3 and 5 that handle 16 defines a cam surface 86 which determines the distance between the pin 58 and the outer surface of the housing upper wall 22. When the handle 16 is in the unlocked position shown in FIG. 5, the pin 58 is relatively close to the wall 22. When the handle 16 is moved to the locked position (FIG. 3), the cam surface 86 bearing against the outer surface of wall 22 pulls the pin further away from the wall 22. This action pulls the rod 68 axially upward through the shaft passageway 66 as the pin 58 moves axially in the elongated shaft holes 62.

Note in FIGS. 2, 4 and 6 that a coil spring 90 is mounted on rod 68 for bearing against the lower end of shaft 36 and the upper face of flange 70 tending to urge them apart. When in the position (FIGS. 3 and 4), the spring 90 is compressed by the upward axial movement of rod flange 70 and the rotatable detent member 76 is forced by the upward movement of radial finger 72 in keyway 74 into firm engagement with the fixed detent member 82. When in the unlocked position (FIGS. 5 and 6), the rod 68 drops downwardly thus relieving the axial force of the radial finger 72 against the rotatable detent member 76. Consequently, the rotatable detent member 76 is able to move axially slightly against a light force applied by coil spring 90 to shoulder 92. This axial spring force is sufficiently light to permit the rotatable detent member 76 to exhibit small amounts of axial movement as it rotates relative to the fixed detent member to allow the respective V-shaped teeth to move past each other.

From the foregoing, it should now be apparent that a ratchet mechanism has been described herein including a pinion assembly which can be selectively placed in a locked state or an unlocked state. When in the unlocked state, a user is able to manually rotate a handle to bidirectionally move an elongate rack while providing discrete step tactile feedback to the user. Although only a single preferred embodiment has been described in detail, it is recognized that modifications and alternative arrangements will readily occur to those skilled in the art which embody the significant aspects of the invention and come within the intended scope of the appended claims.

The invention claimed is:

1. A manually operable ratchet mechanism comprising: a housing; an elongate rack mounted for bidirectional movement relative to said housing; a shaft mounted on said housing for axial rotation; a handle coupled to said shaft for manually axially rotating said shaft; a pinion carried by said shaft configured for engagement with said rack; said handle mounted for pivotal movement around a pivot axis oriented substantially perpendicular to said shaft between a locked position and an unlocked position; and a locking member coupled to said handle for inhibiting rotation of said shaft when said handle is in said locked position, wherein the locking member is movable relative to the shaft.

2. The mechanism of claim 1 wherein said locking member is mounted for axial movement between a first position when said handle is in said unlocked position and a second position when said handle is in said locked position.

3. The mechanism of claim 2 further including a detent member coupled to said shaft for rotation therewith; and wherein said locking member in said second position firmly engages said detent member to inhibit rotation thereof.

4. The mechanism of claim 2 further including: a fixed detent member fixedly located relative to said housing; a rotatable detent member coupled to said shaft for rotation relative to said fixed detent member, said rotatable detent member and said fixed detent member being configured to cooperatively define a series of discrete detent positions; and wherein said locking member in said second position firmly engages said rotatable detent member with said fixed detent member to inhibit rotation of the shaft.

5. The mechanism of claim 4 wherein at least one of said detent members includes a series of V-shaped teeth.

6. The mechanism of claim 2 wherein said handle includes a cam surface configured to axially move said locking member when said handle is moved between said locked and unlocked positions.

7. A manually operable ratchet mechanism including:
a pinion mounted for rotation relative to a longitudinal axis;
a first detent member mounted for rotation relative to said longitudinal axis;
a second detent member fixedly mounted relative to said first detent member for cooperative engagement therewith;
a handle means operable in an unlocked position for manually rotating said pinion and said first detent member and operable in a locked position for inhibiting such rotation;
a locking member for engaging said first detent member with said second fixed detent member to inhibit rotation of the pinion when said handle member is in said locked position, the locking member being movable relative to the pinion; and wherein said first and second detent members are cooperatively configured to define a series of discrete detent positions as said first detent member rotates relative to said fixedly mounted second detent member.

8. The mechanism of claim 7 further including: a spring for urging said first and second detent members into engagement when said handle member is in said unlocked position.

9. The mechanism of claim 8 wherein said handle member is mounted for pivotal movement around a pivot axis oriented substantially perpendicular to said longitudinal axis between said unlocked position and said locked position.

10. The mechanism of claim 9 wherein said handle includes a cam surface configured to axially move said locking member when said handle is moved between said locked and unlocked positions.

11. The mechanism of claim 8 wherein at least one of said detent members includes a series of V-shaped teeth.

12. The mechanism of claim 1 wherein said shaft has an opening extending therethrough and said locking member is slidable disposed within said opening.

13. The mechanism of claim 12 wherein said handle includes a cam surface configured to axially move said locking member when said handle is moved between said locked and unlocked positions.

14. The mechanism of claim 13 further including:
a fixed detent member fixedly attached to said housing;
a rotatable detent member coupled to said shaft for rotation relative to said fixed detent member, wherein said locking member in said second position firmly engages said rotatable detent member with said fixed detent member to inhibit rotation of the shaft.

15. A manually operable ratchet mechanism comprising:
a housing;
an elongate rack mounted for bidirectional movement relative to the housing;
a shaft mounted on the housing for axial rotation, the shaft having an opening extending therethrough;
a pinion carried by the shaft configured for engagement with the rack;
a handle coupled to the shaft for manually axially rotating the shaft, the handle being mounted for pivotal movement around a pivot axis oriented substantially perpendicular to the shaft between a locked position and an unlocked position; and
a locking member disposed within the opening of the shaft, the locking member being coupled to the handle to inhibit rotation of the shaft when the handle is in the locked position.

16. The mechanism of claim 15 wherein the handle includes a cam surface configured to move the locking member relative to the shaft when the handle is moved between the locked and unlocked positions.

17. The mechanism of claim 16 further including:
a fixed detent member fixedly attached to the housing;
a rotatable detent member coupled to the shaft for rotation relative to the fixed detent member, wherein the locking member in the second position engages the rotatable detent member with the fixed detent member to inhibit rotation of the shaft.

18. The mechanism of claim 15 wherein the shaft includes an axially elongated hole, the locking member includes a through hole and the handle includes a pair of ears having ear holes, the mechanism including a pin which extends through the ear holes of the handle, the through hole of the locking member and the axially elongated hole of the shaft.

19. The mechanism of claim 17 further including:
a spring for urging the rotatable detent member towards the fixed detent member when the handle member is in said unlocked position.

20. The mechanism of claim 17 wherein:
the rotatable detent member includes a keyway and the locking member includes a finger which is movable in the keyway when the locking member moves between the locked and unlocked positions.

\* \* \* \* \*